(12) United States Patent
Wilhelm

(10) Patent No.: US 9,904,831 B2
(45) Date of Patent: Feb. 27, 2018

(54) METHOD OF DETECTING THE POSITION OF A CASSETTE AND ITS DEVICE

(71) Applicant: DREAMPATH DIAGNOSTICS, Strasbourg (FR)

(72) Inventor: Valerie Wilhelm, Illkirch-Graffenstaden (FR)

(73) Assignee: Dreampath Diagnostics, Strasbourg (FR)

( * ) Notice: Subject to any disclaimer, the term of this patent is extended or adjusted under 35 U.S.C. 154(b) by 0 days.

(21) Appl. No.: 15/022,187

(22) PCT Filed: Sep. 16, 2014

(86) PCT No.: PCT/FR2014/052297
§ 371 (c)(1),
(2) Date: Mar. 15, 2016

(87) PCT Pub. No.: WO2015/040320
PCT Pub. Date: Mar. 26, 2015

(65) Prior Publication Data
US 2016/0232391 A1 Aug. 11, 2016

(30) Foreign Application Priority Data
Sep. 17, 2013 (FR) ...................................... 13 58925

(51) Int. Cl.
*G07F 17/00* (2006.01)
*G06K 7/14* (2006.01)
(Continued)

(52) U.S. Cl.
CPC ........ *G06K 7/1413* (2013.01); *A61B 10/0096* (2013.01); *G06K 7/10554* (2013.01); *G07F 11/62* (2013.01); *G07F 17/0092* (2013.01)

(58) Field of Classification Search
CPC .............. G06K 7/1413; G06K 7/10554; A61B 10/0096; G07F 11/62; G07F 17/0092
See application file for complete search history.

(56) References Cited

U.S. PATENT DOCUMENTS

| 2007/0135965 A1 | 6/2007 | Nguyen |
| 2007/0185615 A1 | 8/2007 | Bossi |
| 2008/0035520 A1* | 2/2008 | Caracciolo .......... G06F 19/3462 206/531 |

FOREIGN PATENT DOCUMENTS

| DE | 94 16 270 U1 | 12/1994 |
| FR | 2 985 590 | 7/2013 |
| WO | 2010 004331 A1 | 1/2010 |

* cited by examiner

*Primary Examiner* — Sonji Johnson
(74) *Attorney, Agent, or Firm* — Andrew W. Chu; Craft Chu PLLC

(57) ABSTRACT

The method of detecting and referencing two-dimensional position of a cassette in a drawer of compartments distributed according to columns and rows includes positioning at least one inserted cassette with the upper face turned towards the top within a compartment. Systematic detection of all compartments is performed automatically by verifying the presence of a cassette and by verifying the presence of a cassette within each compartment. The detection can be optical and include displacing an optical sight relatively with respect to the top of the drawer according to at least one trajectory passing through all compartments. When detecting a cassette within a compartment, the two-dimensional position is identified by coordinates, according to column and row. If an error occurs during a first pass, the detection and reading are displaced directly to the position where the error occurrence was noted and previously recorded, without undertaking a new detection of all compartments.

4 Claims, 1 Drawing Sheet

(51) Int. Cl.
*G07F 11/62* (2006.01)
*A61B 10/00* (2006.01)
*G06K 7/10* (2006.01)

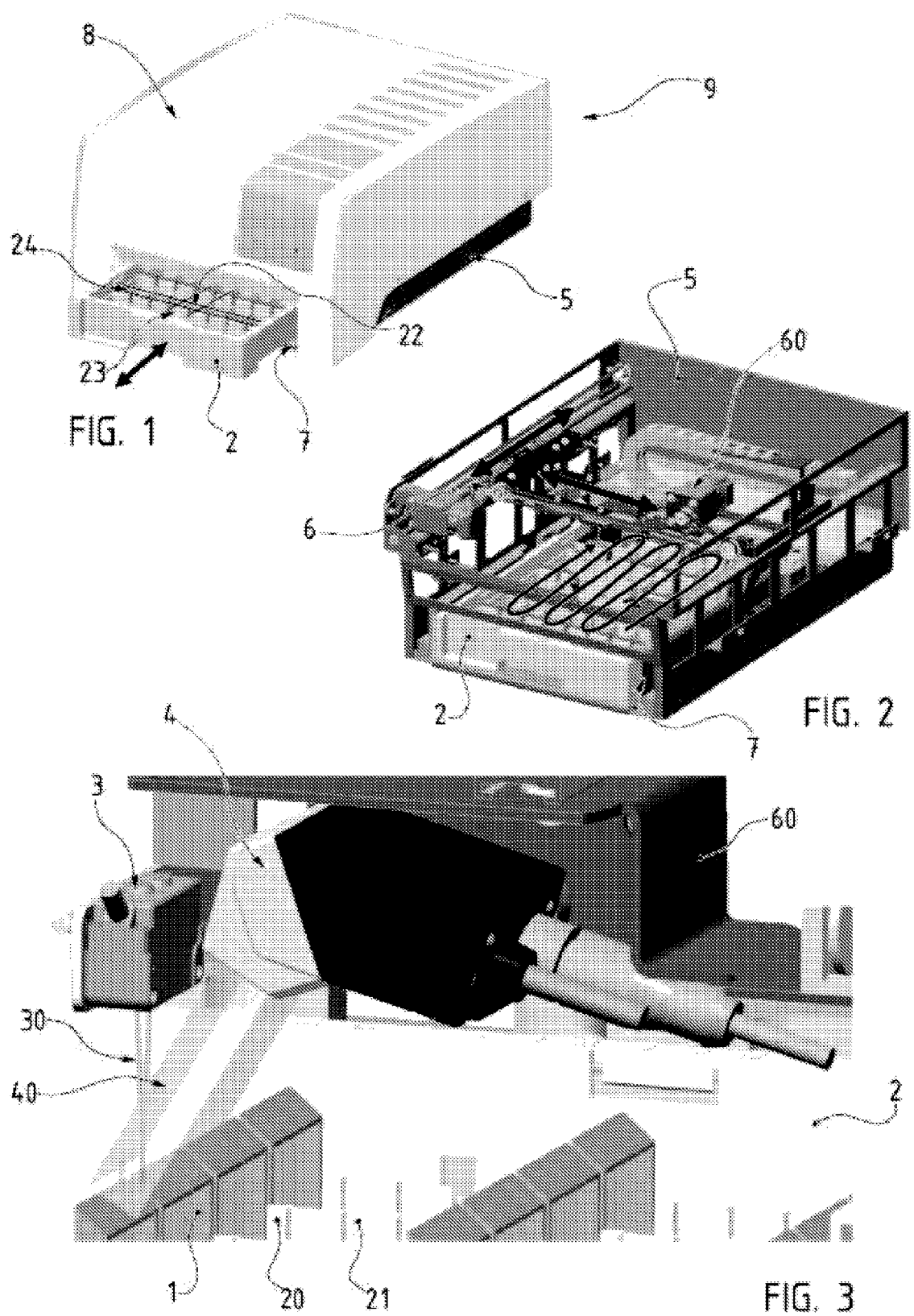

METHOD OF DETECTING THE POSITION OF A CASSETTE AND ITS DEVICE

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

This invention falls within the medical field of tissue and cell sample analysis.

The invention relates more particularly to the preservation and storage of such samples.

2. Description of Related Art Including Information Disclosed Under 37 CFR 1.97 and 37 CFR 1.98.

As part of the medical care of a patient or for research purposes, tissue or cell samples may be taken for histological and/or molecular analysis. For preservation purposes, these specimens are dehydrated and then stored embedded in paraffin in a container commonly known as a "cassette". After preparing the slices of the specimens needed for histological and/or molecular analysis, the tissue and cell residues embedded in paraffin are retained in order to be able to perform further analyses subsequently (sometimes years later).

Such cassettes generally consist of a box in a standardised rectangular parallelepiped shape, with or without a lid, the bottom of which is of an openwork design with through holes. In addition, one of the side walls, generally the front wall has an area for marking with unique identifying information about the specimen, such as a reference number. Such a wall may be provided inclined, in order to facilitate the reading of said information.

Several examples of such cassettes are described in patents U.S. D448 487 S, U.S. Pat. No. 4,421,246 and GB 2 113 249.

These cassettes and their samples are listed and stored by different establishments, in particular medical laboratories. By law, they must be kept for each individual for a period of at least ten years for private companies, and this can reach several decades for a public establishment or the pharmaceutical industry.

Such a cassette is generally of standardised dimensions, with a height of 41.8 millimeters (mm), a width of 28.5 mm and a height or thickness of 6.5 mm.

Currently, said cassettes are stored and handled manually, by operators who have not necessarily been trained and without any controls. As a result, such manual handling leads to errors and a considerable amount of time wasted in looking for them and in some cases even the loss of certain samples.

In addition, in this context, quantities of existing cassettes are constantly growing: from approximately 200 million a year in the 1990s their number had risen to almost 400 million a year by 2010 and is expected to continue growing to reach 750 million a year by 2030. This being the case, the storage capacities and empirical means currently used are not designed to support the management of the rational and secure storage of such quantities.

Therefore, a computerised automated system of organising cassettes of biological specimens has been designed. Such a system seeks to be able to provide traceability and rational management of cassettes, in large numbers, in particular when they are kept in separate geographical locations.

To do this, such a system provides, first of all, means of storing several cassettes, by positioning them in at least one horizontal storage container in the form of a drawer. The latter contains compartments formed by vertical walls extending across the entire width of the drawer, thereby creating several separate columns. The width of the columns corresponds to that of the cassettes to be inserted in them. In addition, each column is subdivided over its entire length into compartments, separated by lugs formed facing one another and protruding orthogonally relative to each wall, extending towards the inside of said column. In addition, said lugs are spaced according to the thickness of a cassette. Each compartment is then able to hold one cassette.

Thus, the cassettes are positioned within the drawer according to columns and rows. In addition, said cassettes are arranged vertically therein, the side containing the identifying information being turned upwards. Such information will be unique to each cassette. It may be recorded in a management system, to provide traceability as well as cross-referencing with the tissue embedded in each cassette and also the patient's medical record.

Furthermore, this identifying information is presented in the form of an optical code, in particular in the form of a barcode or data matrix code, designed to be read by an optical reader, in particular in the form of a light scanner.

Such a system has the advantage of not involving any ordering at the time of placing said cassettes in such a storage device, as the cassettes can be positioned without any precise order of arrangement when filling the columns and rows. The organisation of this particular form of storage results from the automatic means of reading said information present on each cassette and the computerised referencing of the position of said cassette within the storage means.

This system of storing cassettes in the form of a drawer and of organising said cassettes is described in patent FR 2 985 590, which deals in a general manner only with the principle of storage and detection, without envisaging any specific and optimum detection technique.

BRIEF SUMMARY OF THE INVENTION

The invention relates particularly to the specific automatic functioning of the reading and referencing of the cassettes stored within such a drawer. Essentially, the invention aims to perform several successive recognition operations, in order to determine the presence and position of the cassettes present and to identify them. These different identifications are repeated if any errors occur in the detection, with a specific trajectory, so as to optimize the time required for such a scanning operation.

To do this, the invention uses a referencing process that includes, on the one hand, the systematic detection of the presence or absence of a cassette slotted into the compartments in said drawer, and on the other hand, the reading of the data present in code form on each cassette detected and, furthermore, the automatic referencing of the position each cassette detected by means of the coordinates of the compartment in which it is inserted.

In addition, the detection and reading are performed optically by an optical sight and by a light scanner designed to be attached to each other, and mobile relatively with respect to said drawer, reading the codes present on each cassette, with a view to identifying and linking it to its two-dimensional position.

More particularly, said method comprises the following steps:
at least one inserted cassette is positioned, with the upper face turned upwards within a compartment in said drawer;
systematic detection of all the compartments is performed automatically by verifying the presence of a cassette;
a systematic detection of all the compartments is performed automatically by verifying the presence of a cassette in each of said compartments, the detection being optical and consisting in displacing an optical sight relatively with respect to said drawer according to at least one trajectory passing over all the compartments;
Such a method is characterised in that:
in the event of the detection of the presence of a cassette within its compartment, a reading of the data present on said upper face is performed and said cassette is identified;
the two-dimensional position of said cassette, identified by way of the coordinates of its compartment, is referenced, according to its column and row; and in that:
in the event of an error in detection or reading during the first pass, the detection and reading means are displaced directly to the position where the error occurrence was noted and previously recorded, without undertaking a new detection and/or reading of all the other compartments.

According to additional, by no means limiting features, the detection may be optical and may consist in relatively displacing an optical sight above said drawer according to at least one trajectory passing over all the compartments.

Advantageously, the reading may be optical and said data may be encoded in the form of a barcode or data matrix code read by a light scanner.

Preferably, the referencing may include the step of recording the position referenced in connection with the data of each cassette in a management system.

According to one specific embodiment, said method may consist in performing several successive detections and readings of the compartments of said drawer.

In addition, the invention also relates to the detection and referencing means for implementing the method according to the invention.

BRIEF DESCRIPTION OF THE SEVERAL VIEWS OF THE DRAWINGS

Other features and advantages of the invention will become clear from the detailed description that follows of the non-limitative embodiments of the invention, with reference to the figures attached.

FIG. 1 shows a schematic perspective view of a means for implementing the method according to the invention, when inserting or removing a drawer.

FIG. 2 shows a schematic view similar to that of FIG. 1, in which the protective housing of said means has been removed, to reveal the means of reading and referencing the cassettes contained within said drawer.

FIG. 3 shows a schematic side view of a detail of the means of detecting the cassettes and optically reading the identifying information, during one step in the method according to the invention.

DETAILED DESCRIPTION OF THE INVENTION

This invention concerns the detection and referencing of the two-dimensional position of at least one cassette 1, and preferably several, within a drawer 2.

As already mentioned, such cassettes 1 take the form of hollow blocks, designed to receive a sample embedded in paraffin. This block has a rectangular parallelepiped shape, with one side presenting an inclined, bevelled edge. This area is designed to be positioned facing upwards when a cassette 1 is placed in a drawer 2.

Accordingly, said drawer 2 includes compartments 22 distributed according to columns 23 and rows 24.

In the preferred embodiment, as shown in the figures, in order to allow for the vertical positioning of the cassettes 1, facilitating their identification once in place, each drawer includes in its bottom means of interlocking. The latter take the form of protrusions or projections 20, regularly spaced thus forming male and female parts in said bottom into which said cassettes 1 can be slotted. In short, the space between each protrusion or projection 20 constitutes a recess or slot into which a cassette 1 can be slotted.

In the preferred embodiment, said projections 20 are formed to protrude out from the bottom, namely in the lower part of the drawer 2, but also along and on either side of the vertical interior walls 21. The latter are arranged parallel to each other, at regular intervals, so as to define columns 23 within said drawer 2.

It will be noted that the spacing between the protrusions or projections 20 is dimensioned so as to allow the slotting in of each cassette 1, with or without any play, but preferably without play. In the latter case, the width of each space, namely the distance between the opposing surfaces of two consecutive protrusions or projections 20, is virtually equal to the thickness of a cassette 1, within one to several tens of millimeters, offering a minimal amount of play.

According to the example of the cassettes mentioned in the introductory section, the width of a row 24 may be approximately 29 millimeters (mm), preferably 29.2 mm for a block 28.5 mm wide. The spacing between the protrusions or projections 20 may then be approximately 6 mm, preferably 6.6 mm, for a block 6.6 mm thick. Finally, the height of the drawer may be approximately 50 to 60 mm, preferably 53.5 mm, for a cassette 41.8 mm long, whilst the height of the dividing walls 21 may be lower, in particular by at least 10 to 30 mm, thereby allowing the top of the cassettes 1 to extend beyond them and enabling them to be gripped more easily.

In addition, the thickness of said protrusions 20 allows the gripping and extraction, manually or automatically, in particular by a robot, of the cassettes 1. To achieve this, according to a particular embodiment, said protrusions or projections 20 may extend over only a part of the height of each interior dividing wall 21. Preferably, the upper part of each wall 21 is without projections 20, the latter extending only from the bottom up to a height less than that of the side walls 21 which surround it, namely two walls 21 or the sides of said drawer 2.

Advantageously, the invention provides for the detection and referencing of the two-dimensional position of any cassette 1 inserted into the compartments 22 of such a drawer 2.

To do this, first of all, at least one inserted cassette 1, and preferably several, is positioned with its upper face turned upwards within a compartment 22 in said drawer 2.

It will be noted that this position is chosen randomly, as any cassette 1 can be positioned in any free compartment 22, namely one that does not contain a cassette. It is therefore not necessary to fill all the columns 23 and all the rows 24. No order of storage is required.

Consequently, without any prior classification, it is necessary to identify each cassette 1 and to calculate its position within the drawer 2.

To do this, first of all, a systematic detection of all the compartments 22 is performed automatically by verifying the presence of a cassette 1 in each of said compartments 22. In short, a scan is performed in order to verify whether a compartment 22 contains a cassette 1 or not.

To do this, in the preferred embodiment an optical sight 3 is displaced relatively above said drawer 2. The latter emits a beam of light 30, in particular a laser beam, enabling the distance to be measured between its point of emission of emission and the point of reflection. In short, if the laser touches the bottom of the compartment 22 or the top of a cassette 1, then the distance measured will be different. Said sight 3 or related means also allow the presence or absence of a cassette 1 in a compartment 22 to be deducted, based on the distance thus measured.

Then, in a second step, in the event of the detection of the presence of a cassette 1 within its compartment 22, a reading of the data present on said upper face is performed and said cassette 1 is identified;

Accordingly, the reading is designed to be optical and said data will then be encoded in the form of a barcode or data matrix code read by a light scanner 4. The latter enables a light beam 40 to be emitted and a reflected beam to be received, enabling the code present on each cassette 1 to be detected.

It will be noted that this reading takes place simultaneously with the detection phase, namely compartment 22 by compartment 22 in succession. In addition, the reading may be performed by emitting and receiving the light beam continuously or at regular intervals, in particular between time lapses corresponding to the relative displacement from one compartment 22 to another.

According to one specific characteristic, the movement of the sight 3 and the scanner 4 may take place relatively with respect to said drawer 2. In other words, in the preferred embodiment, they may move in relation to the drawer 2, but in another embodiment envisaged, it is the drawer 2 that can move in relation to the sight 3 and the scanner 4, with the latter remaining fixed.

In addition, the sight 3 and the scanner 4 may be attached to each other, moving relatively together. In another embodiment envisaged, the sight 3 and the scanner 4 may move separately.

Accordingly, in the preferred embodiment, as can be seen in FIG. 2, the sight 3 and the scanner 4 are mounted jointly mobile in relation to a fixed structure 5. To achieve this, the latter comprises a chassis with at the top means 6 for moving and driving the detection and reading means, namely the sight 3 and the scanner 4. These means 6 include in particular a mobile carriage 7 supporting said sight 3 and scanner 4. Such a carriage 7 is mobile and driven in translation according to at least two degrees of orientation, as schematically illustrated by the arrows visible in FIG. 2.

Furthermore, this movement takes place above the drawer 2, on its open side, towards which the cassettes 1 with their identification data facing upwards are turned.

In particular, the movement may follow a precise trajectory. The latter may consist of starting from a point situated preferably at a corner of the structure 5, to travel over each row 24 or column 23 of the compartment 22 one after the other, in both directions. In particular, this trajectory may follow the columns 23 front to back, then pass across to the adjacent column 23 and follow it from back to front, and so forth until the last column 23. An example of such a trajectory is shown schematically in FIG. 2. Once this trajectory has been completed, following a given path, the means of detection are returned to their original position.

In addition, essentially, several successive paths are envisaged, in particular numbering two, but preferentially three. This double or triple passage enables the systematic reading of all the cassettes 1 and the rectification of any errors in detection and reading that occurred during the previous pass.

It will be noted then that the first pass consists of a trajectory covering the entire drawer 2, namely one that passes over every compartment, whether it contains a cassette 1 or not.

Indeed, in the event of an error in detection or reading, the detection and reading means may be displaced directly to the position where the error occurrence was noted and previously recorded. In short, during the first pass, an error occurs, such as for example when a cassette 1 is detected in a compartment 22, but it is impossible to read its data. The position is recorded so that, during the next pass, the means can be moved to this location first, without undertaking a new detection and/or reading of all the other compartments 22 where these operations took place correctly during the previous pass.

Thus, the invention allows the accurate detection and identification of the cassettes present in the drawer, with an optimum path, even if it has to be repeated. In particular, in the event of a reading error, the detection is repeated directly at the location where the error occurred, without repeating the entire previous path, in particular the first path that covers the entire drawer.

Accordingly, the relative movements of the detection and reading means may be performed according to the drawer 2, namely according to steps corresponding to the distance between two compartments 22 in the same column 23 or between two rows 24, as well as at both ends of the latter, and according to another step corresponding to the reciprocal distance between two columns 23 or two compartments 22. These steps are therefore determined and specific to the dimensions of each of said drawers 2.

In addition, it is these steps that enable said detection and reading means to tell the exact position, according to a two-dimensional mark.

In another embodiment envisaged, the position may be detected, in particular by reading a mark on said drawer 2, the latter featuring a code that can be read and corresponding to the two-dimensional position, based on a column 23 and a row 24.

In both cases, these coordinates include at least two variables, and may take the following form for example: A1, A2 . . . , B1, B2 . . . where the letters A, B, etc. are allocated to the successive columns 23 (or the rows 24) and the digits 1, 2, etc. are allocated to the successive rows 24 (or reciprocally, the columns 23).

A third variable may be added, corresponding to the reference of a drawer 2, each drawer 2 being in this case identified by its own unique reference number, which it is also possible to detect and read with the invention.

Once a cassette 1 has been read, the two-dimensional position of said cassette, identified by way of the coordinates of its compartment 22, is referenced, according to its column 23 and row 24. This referencing may include the step of recording the position referenced in connection with the data of each cassette 1 in a management system.

The latter may be connected directly, or remotely, to the system according to the invention. It can be used in particular to display the detection and reading of the cassettes 1 present within a drawer 2 in real time. In particular, in the event of an error, for example the failure to read the data, the compartment 22 may be represented by a correlating code, in red for example. Similarly, if a detection and reading operation has been performed successfully, the compartment 22 will show another colour, such as green, as well as the unique identifying data of the cassette 1 that is in it.

Furthermore, such a management system may consist of a relational database, able to store all the data recorded, including the cassettes 1 identified and their referenced position, but also any data connected to the operations performed, such as for example statistics on the use of the system, the errors that occur, the number of cycles and passes, etc.

This management system thus offers perfect traceability, accessible locally or remotely, providing the exact location of a cassette 1.

In addition, at the end of a full referencing cycle, a digital photograph can be taken of the drawer 2. In another embodiment, a digital photograph may be taken of each cassette 1 when it is read.

To do this, the invention provides for the embedding with the detection and reading means of a digital camera whose lens is turned towards the open upper face of the drawer 2. Such a camera and the photographs it captures can in particular facilitate for an operator, at a later stage, the operation consisting of finding and removing a cassette 1. Indeed, the latter may be of different colours and, using the photograph and the coordinates, the operator will then be able to identify the relevant cassette 1 that he is looking for more quickly.

These photographs can also provide digital proof of the presence of a cassette 1 at a given time, if the referencing were to fail. To achieve this, each photograph can be time-stamped, and even certified, in particular by means of a digital signature and/or a digital certificate.

Furthermore, the structure 5 enables, in the lower part, at least one drawer 2 to be held, as shown in FIGS. 1 and 2 according to the preferred embodiment. In another embodiment, several drawers 2 can be positioned within the structure 5, said structures 2 being positioned in this case side by side, in the same plane. In a further embodiment envisaged, several drawers 2 can be stacked, the detection and referencing being performed only on the top drawer 2. Then, once the entire top drawer 2 has been scanned and listed, the latter can be automatically shifted or removed from the structure 5, in order to repeat the operation with the drawer 2 situated just underneath, and so forth. This solution allows for the large-scale automation of the referencing process, in particular in the case of a cabinet with at least one pile of drawers 2.

In all these cases, the structure 5 includes in its lower part the means to hold each drawer 2. These means comprise at least one housing 60, formed in such a way as to allow the insertion of a drawer 2, in particular by sliding in a horizontal or substantially horizontal movement. Appropriate means enable said drawer 2 to be locked into said housing 60, in particular during the referencing phase. The locking and unlocking of such means may be performed manually or automatically, in particular throughout the duration of the detection and reading phase, thereby preventing the accidental removal of the drawer 2 during the process.

In addition, said structure 5 may be covered by a shell or protective casing 8, as shown in FIG. 1, serving to protect and limit access to the means it encloses. This shell 8 also serves to limit the penetration of light from outside, thereby improving the optical detection and reading performances.

The invention also relates to the device 9 for implementing the method according to the invention, namely the detection and referencing of the two-dimensional position of at least one cassette within a drawer, said drawer comprising compartments 22 distributed according to columns 23 and rows 24.

Such a device 9 comprises:
  means of holding said drawer 2, open at the top;
  optical means of detecting the presence of a cassette within each compartment 22, in the form of an optical sight 3; and
  optical means of reading the data present on each cassette detected, in the form of a light scanner 4,
  these means being mounted attached to each other and mobile above said drawer 2 and controlled in their movement to cover a trajectory passing over each of said compartments 22.

Said device 9 also comprises means of referencing the position of each cassette 1, detected by means of the coordinates of its compartment 22, according to its column 23 and row 24. It also comprises means of managing the referenced position of each cassette 1 within said drawer 2 and means of recording said position within said management system.

Thus, the system, consisting of the detection and referencing method and device according to the invention, automatically and systematically allows the referencing and listing of cassettes 1, whilst guaranteeing perfect traceability thereof and appropriate storage.

I claim:

1. A method of detecting and referencing two-dimensional position of at least one cassette within a drawer, said drawer comprising compartments distributed according to columns and rows, said method comprising the steps of:
  positioning at least one inserted cassette with an upper face turned upwards within a compartment in said drawer; and
  detecting systematically all compartments automatically by verifying presence of a cassette in each of said compartments, wherein the step of detecting is optical detecting, and wherein the step of detecting comprises displacing an optical sight relatively with respect to a top of said drawer according to at least one trajectory passing over all compartments in a first pass through said drawer, wherein, when a presence of a cassette within a compartment is detected, said method comprises the steps of:
  identifying said cassette by a reading of data present on said upper face; and
  identifying a two-dimensional position of said cassette by way coordinates of said compartment, according to column and row, and wherein, when an error in the step of identifying said cassette or the step of identifying said two-dimensional position occurs during said first pass, said error having a corresponding two-dimensional position of said error, said method comprises the step of:
  repeating the step of identifying said cassette or the step of identifying said two-dimensional position corresponding to said error at the two-dimensional position of said error during said first pass, before repeating the step of detecting systematically all compartments automatically for another pass.

2. The method, according to claim 1, wherein said reading of data is optical by a light scanner, said data being selected from a group consisting of an encoded barcode and a data matrix code.

3. The method, according to claim 1, wherein the step of identifying two-dimensional position further comprises the step:
  recording the two-dimensional position corresponding to said reading of data of each cassette in a management system.

4. The method, according to claim 1, further comprising the step of: repeating the step of detecting systematically all compartments automatically for another pass for the compartments of said drawer.

* * * * *